(12) United States Patent
Kramer et al.

(10) Patent No.: US 10,570,033 B2
(45) Date of Patent: Feb. 25, 2020

(54) WATER TREATMENT

(71) Applicant: BWA WATER ADDITIVES UK LIMITED, Manchester (GB)

(72) Inventors: Jeffrey Frank Kramer, Tucker, GA (US); Christy Colleen Wentworth, Atlanta, GA (US)

(73) Assignee: ITALMATCH CHEMICALS GB LIMITED, Manchester (GB)

( * ) Notice: Subject to any disclaimer, the term of this patent is extended or adjusted under 35 U.S.C. 154(b) by 264 days.

(21) Appl. No.: 15/152,712

(22) Filed: May 12, 2016

(65) Prior Publication Data

US 2017/0327391 A1 Nov. 16, 2017

(51) Int. Cl.
| | |
|---|---|
| *A01N 57/20* | (2006.01) |
| *A01N 57/34* | (2006.01) |
| *A01N 59/08* | (2006.01) |
| *C02F 1/50* | (2006.01) |
| *C02F 1/76* | (2006.01) |
| C02F 103/02 | (2006.01) |
| C02F 103/28 | (2006.01) |
| C02F 103/36 | (2006.01) |
| C02F 103/10 | (2006.01) |

(52) U.S. Cl.
CPC .............. *C02F 1/50* (2013.01); *A01N 57/20* (2013.01); *A01N 57/34* (2013.01); *A01N 59/08* (2013.01); *C02F 1/76* (2013.01); *C02F 2103/023* (2013.01); *C02F 2103/10* (2013.01); *C02F 2103/28* (2013.01); *C02F 2103/365* (2013.01); *C02F 2307/14* (2013.01)

(58) Field of Classification Search
CPC .......... C02F 1/50; C02F 1/76; C02F 2103/10; C02F 2103/28; A01N 57/20; A01N 59/00; A01N 59/08; A01N 31/02; A01N 35/04; C01B 11/023
See application file for complete search history.

(56) References Cited

U.S. PATENT DOCUMENTS

| | | | |
|---|---|---|---|
| 3,281,365 A | 10/1966 | Moedritzer | |
| 4,835,143 A | 5/1989 | Donofrio et al. | |
| 4,874,526 A | 10/1989 | Grade et al. | |
| 5,063,213 A | 11/1991 | Whitekettle et al. | |
| 5,063,214 A | 11/1991 | Whitekettle et al. | |
| 5,063,218 A | 11/1991 | Whitekettle et al. | |
| 5,102,874 A | 4/1992 | Lintner et al. | |
| 5,376,731 A | 12/1994 | Kerr et al. | |
| 5,741,757 A | 4/1998 | Cooper et al. | |
| 6,241,898 B1 | 6/2001 | Wright et al. | |
| 6,419,879 B1 | 7/2002 | Cooper et al. | |
| 6,471,974 B1 | 10/2002 | Rees et al. | |
| 6,478,972 B1 | 11/2002 | Shim et al. | |
| 6,669,904 B1 | 12/2003 | Yang et al. | |
| 2005/0061753 A1 | 3/2005 | Dickinson et al. | |
| 2006/0006121 A1* | 1/2006 | Simpson | C02F 1/76 210/749 |
| 2006/0032823 A1 | 2/2006 | Harrison et al. | |
| 2006/0113251 A1 | 6/2006 | McGuire et al. | |
| 2007/0012632 A1 | 1/2007 | Simons | |
| 2007/0102359 A1* | 5/2007 | Lombardi | B01D 17/085 210/639 |
| 2009/0050320 A1* | 2/2009 | Collins | E21B 43/20 166/266 |
| 2009/0229827 A1 | 9/2009 | Bryant et al. | |
| 2010/0160449 A1* | 6/2010 | Rovison, Jr. | A01N 37/02 514/714 |
| 2010/0200239 A1 | 8/2010 | Aften | |
| 2010/0226874 A1 | 9/2010 | Kramer et al. | |
| 2011/0257788 A1* | 10/2011 | Wiemers | B01D 61/022 700/267 |
| 2012/0024794 A1 | 2/2012 | Fischmann | |
| 2012/0087993 A1* | 4/2012 | Martin | A01N 35/04 424/661 |
| 2012/0178722 A1 | 7/2012 | Yin | |
| 2012/0223022 A1 | 9/2012 | Hassler et al. | |
| 2012/0285693 A1 | 11/2012 | Mirakyan et al. | |
| 2014/0030306 A1 | 1/2014 | Polizzotti et al. | |

(Continued)

FOREIGN PATENT DOCUMENTS

| | | |
|---|---|---|
| EP | 0479465 A2 | 4/1992 |
| EP | 0681995 A1 | 10/1994 |

(Continued)

OTHER PUBLICATIONS

"Wikipedia: Chlorite". (Apr. 2016) https://en.wikipedia.org/w/index.php?title=Chlorite&oldid=713065886 (Year: 2016).*

"Wikipedia: Sodium Chlorite". (Mar. 2016) https://en.wikipedia.org/w/index.php?title=Sodium_chlorite&oldid=708458222 (Year: 2016).*

BWA Water Additives, "Product Label for Bellacide® 303," http://www.kellysolutions.com/erenewals/documentsubmit/KellyData%5COK%5Cpesticide%5CProduct%20Labe1%5C83451%5C83451-20%5C83451-20 Bellacide 303 6 16 2011_2_54_43_PM.pdf, 1 page (2006).

(Continued)

*Primary Examiner* — Lucas A Stelling
(74) *Attorney, Agent, or Firm* — McNees Wallace & Nurick LLC

(57) ABSTRACT

The present invention relates to water treatment. In one example, there is provided a method of treating an aqueous system to inhibit growth of one or more micro-organisms therein and/or to reduce the number of live micro-organisms therein. The method includes adding treatment agents to an aqueous system wherein said treatment agents include:
(a) a phosphonium compound; and
(b) a compound having formula:

$$M(XO_2)_n$$

wherein:
M is a Group I or Group II metal;
X is a halogen; and
n is 1 or 2.

26 Claims, No Drawings

(56) References Cited

U.S. PATENT DOCUMENTS

| | | | | |
|---|---|---|---|---|
| 2014/0166588 | A1* | 6/2014 | Fischmann | C02F 1/76 210/742 |
| 2014/0194335 | A1 | 7/2014 | Gu et al. | |
| 2015/0056648 | A1 | 2/2015 | Tidwell et al. | |
| 2015/0225235 | A1 | 8/2015 | McIlwaine et al. | |
| 2016/0100582 | A1 | 4/2016 | Kramer | |
| 2016/0100584 | A1 | 4/2016 | Kramer | |
| 2016/0102002 | A1 | 4/2016 | Kramer | |
| 2016/0288045 | A1 | 10/2016 | Kramer et al. | |

FOREIGN PATENT DOCUMENTS

| | | |
|---|---|---|
| GB | 2354771 A | 4/2001 |
| JP | 10273408 A | 10/1998 |
| JP | 2010167320 A | 8/2010 |
| WO | 9104668 A1 | 4/1991 |
| WO | 0142145 A1 | 6/2001 |
| WO | 03031347 A1 | 4/2003 |
| WO | 03073848 A1 | 9/2003 |
| WO | 2005123607 A1 | 12/2005 |
| WO | 2010100470 A2 | 9/2010 |

OTHER PUBLICATIONS

BWA Water Additives, "Product Information: Bellacide® 303—Multi-purpose Non-oxidizing Biocide for Industrial Water Systems," http://www.wateradditives.com/Repository/Files/A_Bellacide_303_GP_WF_AsiaPac_0.pdf, 2 pages (2006).

BWA Water Additives, "Technical Data: Bellacide® 303—Multi-purpose Non-oxidizing Biocide for Industrial Water Systems," http://www.wateradditives.com/Repository/Files/BWA_Bellacide_303_TI_WF_AsiaPac.pdf, 4 pages (2006).

Kull et al., "Mixtures of Quaternary Ammonium Compounds and Long-chain Fatty Acids as Antifungal Agents," Applied Microbiology, vol. 9, pp. 538-541 (1961).

May, "Polymeric Antimicrobial Agents," Disinfection, Sterilization, and Preservation, Chapter 18, pp. 322-333, Philadelphia, Lea & Febiger, US (1991).

Rembaum, "Biological Activity of Ionene Polymers", Applied Polymer Symposium No. 22, pp. 299-317 (1973).

Giri et al., "Effluents from Paper and Pulp Industries and their impact on soil properties and chemical composition of plants in Uttarakhand, India", Journal of Environment and Waste Management, vol. 1, pp. 26-32 (2014).

Kramer et al., "A New High Performance Quaternary Phosphonium Biocide for Microbiological Control in Oilfield Water Systems", NACE International Corrosion Conference & Expo, Paper No. 08660 (2008).

Kim et al. "Isolation and Culture Conditions of a Klebsiella pneumoniae Strain That Can Utilize Ammonium and Nitrate Ions Simultaneously with Controlled Iron and Molybdate Ion Concentrations", Biosci. Biotechnol. Biochem., 66 (5), 996-1001, 2002.

Augustinovic et al., "Microbes—Oilfield Enemies or Allies?" Oilfield Review, Summer 2012:24, No. 2, pp. 4-17, 2012.

Braunstein et al., "Indole-positive Strains of Klebsiella pneumoniae Producing Hydrogen Sulfide in Iron-Agar Slants", downloaded from https://academic.oup.com/ajcp/article-abstract/65/5/702/1765452, Dec. 19, 2017.

Abdou, "Finding Value in Formation Water", Oilfield Review Spring 2011:23, No. 1, pp. 24-35, 2011.

Grab et al., "The Effect of Process Leak Contaminants on Biocidal Efficacy", 1994 Cooling Tower Institute Annual Meeting, Houston, TX, 8 pages, Feb. 1994.

McCoy, "Microbiology of Cooling Water", Chemical Publishing Co., Inc., pp. 76-77, 1980.

Chemical Reactivity of ClO2, Chlorine Dioxide Chemistry, Scotmas, available at http://www.scotmas.com/chlorine-dioxide/chemical-reactivity-of-clo2.aspx?locale=en, Apr. 24, 2018.

"Red-Oxy: Method of Treating Oilfield Water", Water Technology & Chemicals, Technical Datasheet, 3 pages, available at https://www.watchwater.de/documents/redoxy_oilfield_water.pdf, Dec. 15, 2017.

Muyzer, et al., "The ecology and biotechnology of sulphate-reducing bacteria", Nature Reviews, Microbiology, vol. 6, pp. 441-454, Jun. 2008.

Akyon, "Biological Treatment of Hydraulic Fracturing Produced Water", University of Pittsburgh Dissertation, 2017.

Zehr, "Microbes in Earth's aqueous environments", Frontiers in Microbiology, Aquatic Microbiology, Opinion Article, vol. 1, Article 4, pp. 1-2, doi: 10.3389/fmicb.2010.00004, www.frontiersin.org, Jul. 2010.

World Health Organization, "Total dissolved solids in Drinking-water", Background document for development of WHO Guidelines for Drinking-water Quality, 2003.

Haller et al., "Determination of Chlorine Dioxide and Other Active Chlorine Compounds in Water", Analytical Chemistry, vol. 20, No. 7, pp. 639-642, Jul. 1948.

Lange, ed., "Detergents and Cleaners", Hanser/Gardner Publications, Cincinnati, pp. 1-3, 1994.

Kirby et al., "The Organic Chemistry of Phosphorus", Elsevier, New York, pp. 152-153, 1967.

Morrison et al., "Organic Chemistry", Allyn and Bacon, Newton, pp. 100-101, 1987.

Madigan et al., "Brock Biology of Microorganisms", Pearson Education, Upper Saddle River, pp. 66-67, 2003.

Denyer et al., eds., "Mechanisms of Action of Chemical Biocides", Blackwell Scientific Publishing, London, pp. 155-170, 1991.

Block, ed., "Disinfection, Sterilization, and Preservation", Lippincott Williams & Wilkins, Philadelphia, pp. 314-316, 2001.

McIlwaine, "Biocides: Modes of Actions and Implications", presented at Corrosion 2006 TEG 149X TIE, NACE International, Houston, 2006.

\* cited by examiner

WATER TREATMENT

FIELD OF THE INVENTION

The present invention relates to water treatment, particularly though not exclusively, to methods of treating aqueous systems to inhibit growth of micro-organisms.

BACKGROUND TO THE INVENTION

The presence and growth of micro-organisms in aqueous systems, especially in industrial water systems, is a concern. Examples of industrial water systems where micro-organisms are a concern include cooling water systems, pulping and papermaking systems and oil and gas field water systems.

The presence of micro-organisms in industrial water systems may result in the formation of deposits on system surfaces. These deposits or slime can give rise to various problems. In cooling water systems, slime may restrict water flow, reduce heat transfer efficiency, cause corrosion and may be aesthetically unappealing especially if algae are present due to their visible green pigmentation. Corrosion can also occur in industrial water systems in the absence of visible slime through the action of micro-organisms.

In pulp and paper mill systems, slime formed by micro-organisms may cause fouling, plugging, or corrosion of the system. The slime may also break loose and become entrained in the paper produced causing blemishes, holes, tears, and odour in the finished product. The end result may therefore be unusable product and wasted output.

Slime can also be a problem in oil and gas field water systems and may cause energy losses due to increased fluid frictional resistance, formation plugging and corrosion. The slime may harbour a mixture of aerobic and anaerobic bacteria that are responsible for the production of hydrogen sulfide gas. The hydrogen sulfide may cause souring of oil and gas which may reduce the quality of these products and increase treatment costs.

*Pseudomonas aeruginosa* bacteria are commonly present in air, water and soil. These bacteria continually contaminate open cooling water systems, pulping and papermaking systems and oil and gas field water systems and are among the most common slime formers. Slime may be viewed as being a mass of cells stuck together by the cementing action of the gelatinous secretions around each cell. The slime entraps other debris, restricts water flow and heat transfer and may serve as a site for corrosion.

*Chlorella vulgaris* algae are also commonly present in air, water and soil. These algae continually contaminate open cooling water systems and their growth turns the water and surfaces in these systems green. They also provide a food source for bacteria, which can stimulate slime formation, and protozoa which can harbour the pathogenic bacterium *Legionella pneumophila*.

A known method of controlling microbial growth in aqueous systems is to use biocides. While biocides are known to inhibit microbial growth the biocidal effect is generally of limited duration. The effectiveness of known biocides may be rapidly reduced as a result of exposure to negative influences. Negative influences may include temperature, pH or reaction with ingredients present in the system which neutralizes their biocidal effect. Therefore, the use of such biocides may involve continuous or frequent addition and their application at multiple sites or zones in the system to be treated. The cost of the biocide treatment and the labour costs associated with the application of known biocides may therefore be significant.

Known biocides are also highly toxic in the quantities known to be required for effective control of microbial populations. As a result, the amount of biocides that can be safely discharged into the environment may be limited by environmental regulations. Therefore, the need exists for improved methods for controlling microbial growth in aqueous systems.

As noted above, known biocides have a number of limitations including the large quantities of biocides which typically have to be used to achieve the desired biocidal effect and the potential harmful effects on the environment of biocides and therefore reducing the amount necessary for control and thus the quantity released to the environment has many benefits.

Accordingly, the present invention aims to address at least one disadvantage associated with the prior art whether discussed herein or otherwise.

SUMMARY OF THE INVENTION

According to the present invention there is provided a method of treating an aqueous system as set forth in the appended claims. Other features of the invention will be apparent from the claims, and the description which follows.

According to a first aspect of the present invention there is provided a method of treating an aqueous system to inhibit growth of one or more micro-organisms therein and/or to reduce the number of live micro-organisms therein, wherein the method comprises adding treatment agents to an aqueous system and wherein said treatment agents comprise:
(a) a phosphonium compound; and
(b) a compound having formula:

wherein:
M is a Group I or Group II metal;
X is a halogen; and
n is 1 or 2.
Suitably, M is a Group I metal. Suitably M is sodium.
Suitably, X is bromine or chlorine. Suitably, X is chlorine.
Suitably n is 1.
Suitably, compound (b) is $NaClO_2$.
Suitably, the method comprises treating an aqueous system to inhibit growth of anaerobic bacteria and/or to reduce the number of live anaerobic bacteria therein. Suitably, the method comprises treating an aqueous system to inhibit growth of facultative anaerobic bacteria and/or to reduce the number of live facultative anaerobic bacteria therein. Suitably, the method comprises treating an aqueous system to inhibit growth of aerobic bacteria and/or to reduce the number of live aerobic bacteria therein.

Suitably, the aqueous system comprises a mixture of water and other constituents. The aqueous system may contain oil. The aqueous system may comprise an oil and water emulsion. The aqueous system may comprise solids. The aqueous system may comprise suspended solids. The aqueous system may comprise high levels of dissolved solids. The aqueous system may comprise one or more salts, for example sodium chloride. Suitably, the aqueous system consists of a body of water. Suitably, the aqueous system consists of a body of water which comprises water and other constituents, for example dissolved solids.

Suitably, the aqueous system comprises an industrial water system. The aqueous system may consist of industrial water. The aqueous system may consist of industrial water which may comprise water and other constituents. The aqueous system may comprise a cooling water system. The aqueous system may consist of cooling water which may comprise water and other constituents. The aqueous system may comprise a pulping and papermaking system. The aqueous system may consist of pulping and papermaking water which may comprise water and other constituents. The aqueous system may comprise an oil and gas field water system. The aqueous system may consist of oil and gas field water which may comprise water and other constituents. The aqueous system may comprise a well treatment fluid. The aqueous system may consist of well treatment fluid which may comprise water and other constituents.

Suitably, the method comprises treating industrial water to inhibit growth of one or more micro-organisms therein and/or to reduce the number of live micro-organisms therein, wherein the method comprises adding treatment agents to said industrial water. The method may comprise treating cooling water to inhibit growth of one or more micro-organisms therein and/or to reduce the number of live micro-organisms therein, wherein the method comprises adding treatment agents to said cooling water. The method may comprise treating pulping and papermaking water to inhibit growth of one or more micro-organisms therein and/or to reduce the number of live micro-organisms therein, wherein the method comprises adding treatment agents to said pulping and papermaking water. The method may comprise treating oil and gas field water to inhibit growth of one or more micro-organisms therein and/or to reduce the number of live micro-organisms therein, wherein the method comprises adding treatment agents to said oil and gas field water. The method may comprise treating a well treatment fluid to inhibit growth of one or more micro-organisms therein and/or to reduce the number of live micro-organisms therein, wherein the method comprises adding treatment agents to well treatment fluid.

Suitably, the method comprises treating an aqueous system which comprises water in an amount of up to 99% by weight. Suitably, the method comprises treating an aqueous system which comprises water in an amount of up to 98% by weight. Suitably, the method comprises treating an aqueous system which comprises water in an amount of up to 97% by weight. Suitably, the method comprises treating an aqueous system which comprises water in an amount of up to 96% by weight. Suitably, the method comprises treating an aqueous system which comprises water in an amount of up to 95% by weight.

Suitably, the method comprises treating an aqueous system which comprises water and one or more constituents comprising organic liquids, organic solids and/or inorganic solids.

Suitably, the method comprises treating an aqueous system which comprises water and oil. Suitably, the aqueous system comprises oil in an amount of at least 1% by weight, for example at least 2% by weight.

Suitably, the method comprises treating an aqueous system which comprises water and dissolved solids. Suitably, the aqueous system comprises dissolved solids in an amount of at least 1% by weight, for example at least 2% by weight.

Suitably, the method comprises treating an aqueous system which comprises water and dissolved organic solids. Suitably, the aqueous system comprises dissolved organic solids in an amount of at least 1% by weight, for example at least 2% by weight.

Suitably, the method comprises treating an aqueous system which comprises water and dissolved inorganic solids. Suitably, the aqueous system comprises dissolved inorganic solids, for example salts, in an amount of at least 1% by weight, for example at least 2% by weight.

Suitably, the method comprises treating an aqueous system which comprises dissolved solids.

Suitably, the method comprises treating an aqueous system having a total dissolved solids (TDS) of 1000 mg $l^{-1}$ or greater. Suitably, the aqueous system has a total dissolved solids (TDS) of at least 2000 mg $l^{-1}$, for example at least: 3000 mg $l^{-1}$; 4000 mg $l^{-1}$; 5000 mg $l^{-1}$; 6000 mg $l^{-1}$; 7000 mg $l^{-1}$; 8000 mg $l^{-1}$; or 9000 mg $l^{-1}$.

Suitably, the method comprises treating an aqueous system having a total dissolved solids (TDS) of 10,000 mg $l^{-1}$ or greater. Suitably, the aqueous system has a total dissolved solids (TDS) of at least 11,000 mg $l^{-1}$, for example at least: 12,000 mg $l^{-1}$; 13,000 mg $l^{-1}$; 14,000 mg $l^{-1}$; 15,000 mg $l^{-1}$; 16,000 mg $l^{-1}$; 17,000 mg $l^{-1}$; 18,000 mg $l^{-1}$; or 19,000 mg $l^{-1}$.

Suitably, the method comprises treating an aqueous system having a total dissolved solids (TDS) of 20,000 mg $l^{-1}$ or greater. Suitably, the aqueous system has a total dissolved solids (TDS) of at least 21,000 mg $l^{-1}$, for example at least: 22,000 mg $l^{-1}$; 23,000 mg $l^{-1}$; 24,000 mg $l^{-1}$; 25,000 mg $l^{-1}$; 26,000 mg $l^{-1}$; 27,000 mg $l^{-1}$; 28,000 mg $l^{-1}$; or 29,000 mg $l^{-1}$.

Suitably, the method comprises treating an aqueous system having a total dissolved solids (TDS) of 30,000 mg $l^{-1}$ or greater. Suitably, the aqueous system has a total dissolved solids (TDS) of at least 31,000 mg $l^{-1}$, for example at least: 32,000 mg $l^{-1}$; for example at least: 33,000 mg $l^{-1}$; 34,000 mg $l^{-1}$; 35,000 mg $l^{-1}$; 36,000 mg $l^{-1}$; 37,000 mg $l^{-1}$; 38,000 mg $l^{-1}$; 39,000 mg $l^{-1}$; or 40,000 mg $l^{-1}$.

The method may comprise treating an aqueous system having a total dissolved solids (TDS) of 50,000 mg $l^{-1}$ or greater. The aqueous system may have a total dissolved solids (TDS) of at least 60,000 mg $l^{-1}$, for example at least: 70,000 mg $l^{-1}$; 80,000 mg $l^{-1}$; 90,000 mg $l^{-1}$; 100,000 mg $l^{-1}$; 110,000 mg $l^{-1}$; 120,000 mg $l^{-1}$; 130,000 mg $l^{-1}$; 140,000 mg $l^{-1}$; 150,000 mg $l^{-1}$; 160,000 mg $l^{-1}$; 170,000 mg $l^{-1}$; 180,000 mg $l^{-1}$; 190,000 mg $l^{-1}$; 200,000 mg $l^{-1}$; 210,000 mg $l^{-1}$; 220,000 mg $l^{-1}$; 230,000 mg $l^{-1}$; 240,000 mg $l^{-1}$; or 250,000 mg $l^{-1}$; 260,000 mg $l^{-1}$; 270,000 mg $l^{-1}$; 280,000 mg $l^{-1}$; 290,000 mg $l^{-1}$; 300,000 mg $l^{-1}$.

Suitably, the method comprises treating an aqueous system having a total dissolved solids (TDS) of 250,000 mg $l^{-1}$ or less. The aqueous system may have a total dissolved solids (TDS) of no more than 240,000 mg $l^{-1}$, for example no more than 230,000 mg $l^{-1}$; 220,000 mg $l^{-1}$; 210,000 mg $l^{-1}$; 200,000 mg $l^{-1}$; 190,000 mg $l^{-1}$; 180,000 mg $l^{-1}$; 170,000 mg $l^{-1}$; 160,000 mg $l^{-1}$; 150,000 mg $l^{-1}$; 140,000 mg $l^{-1}$; 130,000 mg $l^{-1}$; 120,000 mg $l^{-1}$; or 110,000 mg $l^{-1}$.

Suitably, the method comprises treating an aqueous system having a total dissolved solids (TDS) of 100,000 mg $l^{-1}$ or less. The aqueous system may have a total dissolved solids (TDS) of no more than 90,000 mg $l^{-1}$, for example no more than 80,000 mg $l^{-1}$; 70,000 mg $l^{-1}$; 60,000 mg $l^{-1}$; 50,000 mg $l^{-1}$; or 40,000 mg $l^{-1}$.

Suitably, the method comprises treating an aqueous system having a total dissolved solids (TDS) of at least 25,000 mg $l^{-1}$. Suitably, the method comprises treating an aqueous system having a total dissolved solids (TDS) of at least 30,000 mg $l^{-1}$.

Suitably, the method comprises treating an aqueous system having a total dissolved solids (TDS) of from 10,000 mg $l^{-1}$ to 300,000 mg $l^{-1}$. Suitably, the method comprises treating an aqueous system having a total dissolved solids (TDS) of from 10,000 mg $l^{-1}$ to 100,000 mg $l^{-1}$. Suitably, the aqueous system has a total dissolved solids (TDS) of from 20,000 mg l$^{-1}$ to 100,000 mg l$^{-1}$, for example from 25,000 mg l$^{-1}$ to 100,000 mg l$^{-1}$. Suitably, the aqueous system has a total dissolved solids (TDS) of from 30,000 mg l$^{-1}$ to 100,000 mg l$^{-1}$. Suitably, the method comprises treating an aqueous system having a total dissolved solids (TDS) of from 20,000 mg l$^{-1}$ to 80,000 mg l$^{-1}$, for example from 25,000 mg l$^{-1}$ to 80,000 mg l$^{-1}$. Suitably, the method comprises treating an aqueous system having a total dissolved solids (TDS) of from 30,000 mg l$^{-1}$ to 80,000 mg l$^{-1}$.

Suitably, the method comprises treating an aqueous system comprising dissolved salts in an amount of 1000 mg l$^{-1}$ or greater. Suitably, the aqueous system comprises dissolved salts in an amount of at least 2000 mg l$^{-1}$, for example at least: 3000 mg l$^{-1}$; 4000 mg l$^{-1}$; 5000 mg l$^{-1}$; 6000 mg l$^{-1}$; 7000 mg l$^{-1}$; 8000 mg l$^{-1}$; or 9000 mg l$^{-1}$.

Suitably, the method comprises treating an aqueous system comprising dissolved salts in an amount 10,000 mg l$^{-1}$ or greater. Suitably, the aqueous system comprises dissolved salts in an amount of at least 11,000 mg l$^{-1}$, for example at least: 12,000 mg l$^{-1}$; 13,000 mg l$^{-1}$; 14,000 mg l$^{-1}$; 15,000 mg l$^{-1}$; 16,000 mg l$^{-1}$; 17,000 mg l$^{-1}$; 18,000 mg l$^{-1}$; or 19,000 mg l$^{-1}$.

Suitably, the method comprises treating an aqueous system comprising dissolved salts in an amount of 20,000 mg l$^{-1}$ or greater. Suitably, the aqueous system comprises dissolved salts in an amount of at least 21,000 mg l$^{-1}$, for example at least: 22,000 mg l$^{-1}$; 23,000 mg l$^{-1}$; 24,000 mg l$^{-1}$; 25,000 mg l$^{-1}$; 26,000 mg l$^{-1}$; 27,000 mg l$^{-1}$; 28,000 mg l$^{-1}$; or 29,000 mg l$^{-1}$.

Suitably, the method comprises treating an aqueous system comprising dissolved salts in an amount of 30,000 mg l$^{-1}$ or greater. Suitably, the aqueous system comprises dissolved salts in an amount of at least 31,000 mg l$^{-1}$, for example at least: 32,000 mg l$^{-1}$; for example at least: 33,000 mg l$^{-1}$; 34,000 mg l$^{-1}$; 35,000 mg l$^{-1}$; 36,000 mg l$^{-1}$; 37,000 mg l$^{-1}$; 38,000 mg l$^{-1}$; 39,000 mg l$^{-1}$; or 40,000 mg l$^{-1}$.

The method may comprise treating an aqueous system comprising dissolved salts in an amount of 50,000 mg l$^{-1}$ or greater. The aqueous system may comprise dissolved salts in an amount of at least 60,000 mg l$^{-1}$, for example at least: 70,000 mg l$^{-1}$; 80,000 mg l$^{-1}$; 90,000 mg l$^{-1}$; 100,000 mg l$^{-1}$; 110,000 mg l$^{-1}$; 120,000 mg l$^{-1}$; 130,000 mg l$^{-1}$; 140,000 mg l$^{-1}$; 150,000 mg $^{-1}$; 160,000 mg l$^{-1}$; 170,000 mg l$^{-1}$; 180,000 mg l$^{-1}$; 190,000 mg l$^{-1}$; 200,000 mg l$^{-1}$; 210,000 mg l$^{-1}$; 220,000 mg l$^{-1}$; 230,000 mg l$^{-1}$; 240,000 mg l$^{-1}$; or 250,000 mg l$^{-1}$; 260,000 mg l$^{-1}$; 270,000 mg l$^{-1}$; 280,000 mg l$^{-1}$; 290,000 mg l$^{-1}$; 300,000 mg l$^{-1}$.

Suitably, the method comprises treating an aqueous system comprising dissolved salts in an amount of 250,000 mg l$^{-1}$ or less. The aqueous system may comprise dissolved salts in an amount of no more than 240,000 mg l$^{-1}$, for example no more than 230,000 mg l$^{-1}$; 220,000 mg l$^{-1}$; 210,000 mg l$^{-1}$; 200,000 mg l$^{-1}$; 190,000 mg l$^{-1}$; 180,000 mg l$^{-1}$; 170,000 mg l$^{-1}$; 160,000 mg l$^{-1}$; 150,000 mg l$^{-1}$; 140,000 mg l$^{-1}$; 130,000 mg l$^{-1}$; 120,000 mg l$^{-1}$; or 110,000 mg l$^{-1}$.

Suitably, the method comprises treating an aqueous system comprising salts in an amount of 100,000 mg l$^{-1}$ or less. The aqueous system may comprise salts in an amount of no more than 90,000 mg l$^{-1}$, for example no more than 80,000 mg l$^{-1}$; 70,000 mg l$^{-1}$; 60,000 mg l$^{-1}$; 50,000 mg l$^{-1}$; or 40,000 mg l$^{-1}$.

Suitably, the method comprises treating an aqueous system comprising dissolved salts in an amount of at least 25,000 mg l$^{-1}$. Suitably, the method comprises treating an aqueous system comprising dissolved salts in an amount of at least 30,000 mg l$^{-1}$.

Suitably, the method comprises treating an aqueous system comprising dissolved salts in an amount of from 10,000 mg l$^{-1}$ to 300,000 mg l$^{-1}$. Suitably, the method comprises treating an aqueous system comprising dissolved salts in an amount of from 10,000 mg l$^{-1}$ to 100,000 mg l$^{-1}$. Suitably, the aqueous system comprises dissolved salts in an amount of from 20,000 mg l$^{-1}$ to 100,000 mg l$^{-1}$, for example from 25,000 mg l$^{-1}$ to 100,000 mg l$^{-1}$. Suitably, the aqueous system comprises dissolved salts in an amount of from 30,000 mg l$^{-1}$ to 100,000 mg l$^{-1}$. Suitably, the method comprises treating an aqueous system comprising dissolved salts in an amount of from 20,000 mg l$^{-1}$ to 80,000 mg l$^{-1}$, for example from 25,000 mg l$^{-1}$ to 80,000 mg l$^{-1}$. Suitably, the method comprises treating an aqueous system comprising dissolved salts in an amount of from 30,000 mg l$^{-1}$ to 80,000 mg l$^{-1}$.

Suitably, the method comprises treating an aqueous system to inhibit the growth of a plurality of different micro-organisms.

Suitably, the method comprises treating an aqueous system to prevent the growth of one or more micro-organisms. Suitably, the method comprises treating an aqueous system to prevent the growth of a plurality of different micro-organisms.

Suitably, the method comprises treating an aqueous system to kill one or more micro-organisms. Suitably, the method comprises treating an aqueous system to kill a plurality of different micro-organisms.

Suitably, the method comprises treating an aqueous system to inhibit or prevent the growth of one or more micro-organisms therein and/or to reduce the number of live micro-organisms therein, wherein said micro-organisms are selected from bacteria, fungi and algae. Suitably, the method comprises a method of inhibiting growth of bacteria and/or killing bacteria. Suitably, the method comprises a method of inhibiting growth of fungi and/or killing fungi. Suitably, the method comprises a method of inhibiting growth of algae and/or killing algae.

Suitably, the method comprises treating an aqueous system to inhibit or prevent the growth of anaerobic micro-organisms. Suitably, the method comprises treating an aqueous system to kill anaerobic micro-organisms. Suitably, the method comprises treating an aqueous system to inhibit or prevent the growth of anaerobic bacteria. Suitably, the method comprises treating an aqueous system to kill anaerobic bacteria. Suitably, the method comprises treating an aqueous system to inhibit or prevent the growth of facultative anaerobic bacteria. Suitably, the method comprises treating an aqueous system to kill facultative anaerobic bacteria.

Suitably, the method comprises treating an aqueous system to inhibit or prevent the growth of facultative anaerobic bacteria and anaerobic bacteria. Suitably, the method comprises treating an aqueous system to kill facultative anaerobic bacteria and anaerobic bacteria.

Suitably, the method comprises treating an aqueous system to inhibit or prevent the growth of aerobic micro-organisms. Suitably, the method comprises treating an aqueous system to kill aerobic micro-organisms. Suitably, the method comprises treating an aqueous system to inhibit or prevent the growth of aerobic bacteria. Suitably, the method comprises treating an aqueous system to kill aerobic bacteria.

Suitably, the method comprises treating an aqueous system to inhibit or prevent the growth of anaerobic and aerobic micro-organisms. Suitably, the method comprises treating an aqueous system to kill anaerobic and aerobic micro-organisms. Suitably, the method comprises treating an aqueous system to inhibit or prevent the growth of anaerobic and aerobic bacteria. Suitably, the method comprises treating an aqueous system to kill anaerobic and aerobic bacteria.

The method may comprise a method of inhibiting growth of gram-positive aerobic bacteria, gram-positive facultative anaerobic bacteria, gram-negative aerobic bacteria, gram-negative facultative anaerobic bacteria, gram-positive anaerobic bacteria and/or gram-negative anaerobic bacteria. The method may comprise a method of inhibiting growth of mold and/or yeast. The method may comprise a method of inhibiting the growth of blue green algae and/or green algae. Suitably, the method comprises a method of inhibiting the growth of gram-negative aerobic bacteria, gram-negative facultative anaerobic bacteria, gram-negative anaerobic bacteria, and green algae. Suitably, the method comprises inhibiting the growth of *Pseudomonas aeruginosa* bacteria in an aqueous system. Suitably, the method comprises inhibiting the growth of *Enterobacter aerogenes* bacteria in an aqueous system. Suitably, the method comprises inhibiting the growth of *Desulfovibrio vulgaris* bacteria in an aqueous system. Suitably, the method comprises inhibiting the growth of *Chlorella vulgaris* algae in an aqueous system.

Suitably, the method comprises adding compounds (a) and (b) to an aqueous system such that a Log10 reduction of 1 or greater in a facultative anaerobe culture is obtained after a contact time of 24 hours. Suitably, the method comprises obtaining a Log10 reduction of 2 or greater to a facultative anaerobe culture after a contact time of 24 hours; for example of 3 or greater; 4 or greater; 5 or greater; or 6 or greater.

Suitably, the method comprises adding compounds (a) and (b) to an aqueous system such that a complete kill of a facultative anaerobe culture is obtained after a contact time of 24 hours.

Suitably, the method comprises adding compounds (a) and (b) to an aqueous system such that a Log10 reduction of 1 or greater in a facultative anaerobe culture is obtained after a contact time of 4 hours. Suitably, the method comprises obtaining a Log10 reduction of 2 or greater to a facultative anaerobe culture after a contact time of 4 hours; for example of 3 or greater; 4 or greater; 5 or greater; or 6 or greater.

Suitably, the method comprises adding compounds (a) and (b) to an aqueous system such that a complete kill of a facultative anaerobe culture is obtained after a contact time of 4 hours. Suitably, the method comprises adding compounds (a) and (b) to an aqueous system such that a complete kill of a facultative anaerobe culture is obtained after a contact time of no more than 4 hours.

Suitably, the method comprises adding compounds (a) and (b) to an aqueous system such that a Log10 reduction of 1 or greater in a facultative anaerobe culture is obtained after a contact time of 1 hour. Suitably, the method comprises obtaining a Log10 reduction of 2 or greater to a facultative anaerobe culture after a contact time of 1 hours; for example of 3 or greater; 4 or greater; 5 or greater; or 6 or greater.

Suitably, the method comprises adding compounds (a) and (b) to an aqueous system such that a complete kill of a facultative anaerobe culture is obtained after a contact time of 1 hour. Suitably, the method comprises adding compounds (a) and (b) to an aqueous system such that a complete kill of a facultative anaerobe culture is obtained after a contact time of no more than 1 hour. Suitably, the method comprises adding compounds (a) and (b) to an aqueous system such that a complete kill of a facultative anaerobe culture is obtained after a contact time of at least 1 hour.

Suitably, the method comprises adding compounds (a) and (b) to an aqueous system such that a complete kill of a facultative anaerobe culture is obtained after a contact time of between 1 and 4 hours.

Suitably, the method comprises adding compounds (a) and (b) to an aqueous system such that a Log10 reduction of 1 or greater in an anaerobe culture is obtained after a contact time of 24 hours. Suitably, the method comprises obtaining a Log10 reduction of 2 or greater to an anaerobe culture after a contact time of 24 hours; for example of 3 or greater; 4 or greater; or 5 or greater.

Suitably, the method comprises adding compounds (a) and (b) to an aqueous system such that a complete kill of an anaerobe culture is obtained after a contact time of 24 hours.

Suitably, the method comprises adding compounds (a) and (b) to an aqueous system such that a Log10 reduction of 1 or greater in an anaerobe culture is obtained after a contact time of 4 hours. Suitably, the method comprises obtaining a Log10 reduction of 2 or greater to an anaerobe culture after a contact time of 4 hours; for example of 3 or greater; 4 or greater; or 5 or greater.

Suitably, the method comprises adding compounds (a) and (b) to an aqueous system such that a complete kill of an anaerobe culture is obtained after a contact time of 4 hours.

Suitably, the method comprises adding compounds (a) and (b) to an aqueous system such that a Log10 reduction of 1 or greater in an anaerobe culture is obtained after a contact time of 1 hour. Suitably, the method comprises obtaining a Log10 reduction of 2 or greater to an anaerobe culture after a contact time of 1 hours; for example of 3 or greater; 4 or greater; or 5 or greater.

Suitably, the method comprises adding compounds (a) and (b) to an aqueous system such that a complete kill of an anaerobe culture is obtained after a contact time of 1 hour. Suitably, the method comprises adding compounds (a) and (b) to an aqueous system such that a complete kill of a facultative anaerobe culture is obtained after a contact time of at least 1 hour. Suitably, the method comprises adding compounds (a) and (b) to an aqueous system such that a complete kill of anaerobe culture is obtained after a contact time of no more than 1 hour.

The method may comprise adding compounds (a) and (b) to an aqueous system such that a Log10 reduction of 1 or greater in an aerobe culture is obtained after a contact time of 24 hours. The method may comprise obtaining a Log10 reduction of 2 or greater to an aerobe culture after a contact time of 24 hours; for example of 3 or greater; 4 or greater; 5 or greater.

The method may comprise adding compounds (a) and (b) to an aqueous system such that a Log10 reduction of 1 or greater in an aerobe culture is obtained after a contact time of 4 hours. The method may comprise obtaining a Log 10 reduction of 2 or greater to an aerobe culture after a contact time of 4 hours; for example of 3 or greater; 4 or greater; 5 or greater.

The method may comprise adding compounds (a) and (b) to an aqueous system such that a Log10 reduction of 1 or greater in an aerobe culture is obtained after a contact time of 1 hour. The method may comprise obtaining a Log10 reduction of 2 or greater to an aerobe culture after a contact time of 1 hour; for example of 3 or greater; 4 or greater; 5 or greater.

Suitably, the method comprises adding compound (a) and compound (b) to the aqueous system such that they are added in a combined amount of from 0.1 to 1000 parts by weight per one million parts by weight of said aqueous system (ppm), for example from 1 to 500ppm.

Suitably, the method comprises adding compound (a) and compound (b) to the aqueous system in a combined amount of from 0.1 to 300ppm.

Suitably, the method comprises adding compound (a) and compound (b) to the aqueous system such that they are present in a combined amount of from 0.1 to 1000 parts by weight per one million parts by weight of said aqueous system (ppm), for example from 1 to 500 ppm. Suitably, the method comprises adding compound (a) and compound (b) to the aqueous system such that they are present in a combined amount of from 0.1 to 300 ppm.

As used herein, all references to ppm refer to parts per million by weight unless stated otherwise.

Suitably, the method comprises adding compound (a) and compound (b) to the aqueous system such that they are added in a total amount of from 5 to 500 ppm. Suitably, the method comprises adding compound (a) and compound (b) to the aqueous system such that they are added in a total amount of from 10 to 400 ppm. Suitably, the method comprises adding compound (a) and compound (b) to the aqueous system such that they are added in a total amount of from 15 to 400 ppm, for example 15 to 50 ppm.

Suitably, the method comprises adding a phosphonium compound treatment agent (a) to an aqueous system in an amount of at least 0.1 parts per million (ppm).

Suitably, the method comprises adding a phosphonium compound treatment agent to an aqueous system to provide a treated aqueous system comprising said phosphonium compound in an amount of at least 0.1 parts per million (ppm).

Suitably, the method comprises adding a phosphonium compound to an aqueous system such that it is added in an amount of at least 0.2 ppm. Suitably, the method comprises adding a phosphonium compound to an aqueous system such that it is added in an amount of at least 0.3 ppm, for example at least: 0.4 ppm; 0.5 ppm; 0.6 ppm; 0.7 ppm; 0.8 ppm; 0.9 ppm; or 1.0 ppm.

Suitably, the method comprises adding a phosphonium compound to an aqueous system such that it is added in an amount of at least 1 ppm; for example at least 1.5 ppm; 2.0 ppm; 2.5 ppm; 3.0 ppm; 3.5 ppm; 4.0 ppm; 4.5 ppm; 5.0 ppm; 5.5 ppm; or 6.0 ppm. The method may comprise adding a phosphonium compound to an aqueous system such that it is added in an amount of at least 6 ppm, for example at least: 7 ppm; 8 ppm; 9 ppm; 10 ppm; 11 ppm; 12 ppm. The method may comprise adding a phosphonium compound to an aqueous system such that it is added in an amount of at least 20 ppm, for example at least: 25 ppm; 30 ppm; 35 ppm; 40 ppm; 45 ppm; or 50 ppm.

Suitably, the method comprises adding a phosphonium compound to an aqueous system such that it is present in an active amount of at least 0.2 ppm. Suitably, the method comprises adding a phosphonium compound to an aqueous system such that it is present in an active amount of at least 0.3 ppm, for example at least: 0.4 ppm; 0.5 ppm; 0.6 ppm; 0.7 ppm; 0.8 ppm; 0.9 ppm; or 1.0 ppm. Suitably, the method comprises adding a phosphonium compound to an aqueous system such that it is present in an active amount of at least 1 ppm; for example at least 1.5 ppm; 2.0 ppm; 2.5 ppm; 3.0 ppm; 3.5 ppm; 4.0 ppm; 4.5 ppm; 5.0 ppm; 5.5 ppm; or 6.0 ppm. The method may comprise adding a phosphonium compound to an aqueous system such that it is present in an active amount of at least 6 ppm, for example at least: 7 ppm; 8 ppm; 9 ppm; 10 ppm; 11 ppm; 12 ppm. The method may comprise adding a phosphonium compound to an aqueous system such that it is present in an active amount of at least 20 ppm, for example at least: 25 ppm; 30 ppm; 35 ppm; 40 ppm; 45 ppm; or 50 ppm.

Suitably, the method comprises adding a phosphonium compound treatment agent to an aqueous system to provide a treated aqueous system comprising said phosphonium compound added in an amount of 1 to 20 ppm, for example 1 to 15 ppm. Suitably, the method comprises adding a phosphonium compound treatment agent to an aqueous system to provide a treated aqueous system comprising said phosphonium compound added in an amount of 1 to 10 ppm, for example 2 to 8 ppm.

Suitably, the method comprises adding a phosphonium compound treatment agent to an aqueous system in an amount of not more than 250 ppm, for example not more than 125 ppm.

Suitably, the method may comprise adding a phosphonium compound treatment agent to an aqueous system in an amount of not more than 100 ppm, for example not more than 50 ppm.

Suitably, the method comprises adding a phosphonium compound to an aqueous system such that it is added in an amount of not more than 40 ppm, for example not more than 35 ppm. The method may comprise adding a phosphonium compound to an aqueous system such that it is added in an amount of not more than 30 ppm, for example not more than 25 ppm. The method may comprise adding a phosphonium compound to an aqueous system such that it is added in an amount of not more than 20 ppm; for example not more than: 15 ppm; 10 ppm or 5 ppm.

Suitably, the method comprises adding a phosphonium compound treatment agent to an aqueous system to provide a treated aqueous system comprising said phosphonium compound in an active amount of not more than 250 ppm, for example not more than 125 ppm.

Suitably, the method comprises adding a phosphonium compound treatment agent to an aqueous system to provide a treated aqueous system comprising said phosphonium compound in an active amount of not more than 100 ppm, for example not more than 50 ppm.

Suitably, the method comprises adding a phosphonium compound to an aqueous system such that it is present in an active amount of not more than 40 ppm, for example not more than 35 ppm. The method may comprise adding a phosphonium compound to an aqueous system such that it is present in an amount of not more than 30 ppm, for example not more than; 25 ppm. The method may comprise adding a phosphonium compound to an aqueous system such that it is present in an amount of not more than 20 ppm, for example not more than: 15 ppm; 10 ppm; or 5 ppm.

Suitably, the method comprises adding a phosphonium compound treatment agent to an aqueous system to provide a treated aqueous system comprising said phosphonium compound added in an amount of 5.5 to 7.0 ppm, for example 6.0 to 6.5 ppm, for example 6.25 ppm. Suitably, the method comprises adding a phosphonium compound treatment agent to an aqueous system to provide a treated aqueous system comprising said phosphonium compound added in an amount of 10 to 15 ppm, for example 12 to 13 ppm, or for example 12.5 ppm.

Suitably, the method comprises adding compound (b) treatment agent to an aqueous system in an amount of at least 0.1 ppm.

Suitably, the method comprises adding compound (b) to an aqueous system to provide a treated aqueous system comprising said compound (b) in an amount of at least 0.1 ppm.

Suitably, the method comprises adding compound (b) to an aqueous system such that it is added in an amount of at least 0.5 ppm. Suitably, the method comprises adding compound (b) to an aqueous system such that it is added in an amount of at least 1 ppm, for example at least: 2 ppm; 3 ppm; 4 ppm or 5 ppm.

Suitably, the method comprises adding compound (b) to an aqueous system such that it is added in an amount of greater than 5 ppm. Suitably, the method comprises adding compound (b) to an aqueous system such that it is added in an amount of at least 10 ppm. Suitably, the method comprises adding compound (b) to an aqueous system such that it is added in an amount of at least: 15 ppm, for example at least: 20 ppm; 25 ppm; 30 ppm; 35 ppm or 40 ppm. The method may comprise adding compound (b) to an aqueous system such that it is added in an amount of at least 50 ppm, for example at least: 60 ppm; 70 ppm; 80 ppm; 90 ppm or 100 ppm. The method may comprise adding compound (b) to an aqueous system such that it is added in an amount of at least 150 ppm, for example at least: 200 ppm; 250 ppm; or 300 ppm.

Suitably, the method comprises adding compound (b) to an aqueous system such that it is present in an amount of at least 0.5 ppm. Suitably, the method comprises adding compound (b) to an aqueous system such that it is present in an amount of at least 1 ppm, for example at least: 2 ppm; 3 ppm; 4 ppm or 5 ppm.

Suitably, the method comprises adding compound (b) to an aqueous system such that it is present in an amount of greater than 5 ppm. Suitably, the method comprises adding compound (b) to an aqueous system such that it is present in an amount of at least 10 ppm. Suitably, the method comprises adding compound (b) to an aqueous system such that it is present in an amount of at least: 15 ppm, for example at least: 20 ppm; 25 ppm; 30 ppm; 35 ppm or 40 ppm. The method may comprise adding compound (b) to an aqueous system such that it is present in an amount of at least 50 ppm, for example at least: 60 ppm; 70 ppm; 80 ppm; 90 ppm or 100 ppm. The method may comprise adding compound (b) to an aqueous system such that it is present in an amount of at least 150 ppm, for example at least: 200 ppm; 250 ppm; or 300 ppm.

Suitably, the method comprises adding compound (b) to an aqueous system such that it is added in an amount of not more than 500 ppm. Suitably, the method comprises adding compound (b) to an aqueous system such that it is added in an amount of not more than 400 ppm; for example not more than 300 ppm. The method may comprise adding compound (b) to an aqueous system such that it is added in an amount of not more than 200 ppm, for example not more than 100 ppm.

Suitably, the method comprises adding compound (b) to an aqueous system such that it is present in an amount of not more than 500 ppm. Suitably, the method comprises adding compound (b) to an aqueous system such that it is present in an amount of not more than 400 ppm; for example not more than 300 ppm. The method may comprise adding compound (b) to an aqueous system such that it is present in an amount of not more than 200 ppm, for example not more than 100 ppm.

Suitably, the method comprises adding compound (b) to an aqueous system to provide a treated aqueous system comprising compound (b) in an amount of 1 to 500 ppm, for example 5 to 400 ppm. The method may comprise adding compound (b) to an aqueous system to provide a treated aqueous system comprising compound (b) in an amount of 10 to 300 ppm, for example 10 to 100 ppm.

Suitably, the method comprises adding $NaClO_2$ treatment agent to an aqueous system in an amount of at least 0.1 ppm.

Suitably, the method comprises adding $NaClO_2$ to an aqueous system to provide a treated aqueous system comprising said $NaClO_2$ in an amount of at least 0.1 ppm.

Suitably, the method comprises adding $NaClO_2$ to an aqueous system such that it is added in an amount of at least 0.5 ppm. Suitably, the method comprises adding $NaClO_2$ to an aqueous system such that it is added in an amount of at least 1 ppm, for example at least: 2 ppm; 3 ppm; 4 ppm or 5 ppm.

Suitably, the method comprises adding $NaClO_2$ to an aqueous system such that it is added in an amount of greater than 5 ppm. Suitably, the method comprises adding $NaClO_2$ to an aqueous system such that it is added in an amount of at least 10 ppm. Suitably, the method comprises adding $NaClO_2$ to an aqueous system such that it is added in an amount of at least:

15 ppm, for example at least: 20 ppm; 25 ppm; 30 ppm; 35 ppm or 40 ppm. The method may comprise adding $NaClO_2$ to an aqueous system such that it is added in an amount of at least 50 ppm, for example at least: 60 ppm; 70 ppm; 80 ppm; 90 ppm or 100 ppm. The method may comprise adding $NaClO_2$ to an aqueous system such that it is added in an amount of at least 150 ppm, for example at least: 200 ppm; 250 ppm; or 300 ppm.

Suitably, the method comprises adding $NaClO_2$ to an aqueous system such that it is present in an amount of at least 0.5 ppm. Suitably, the method comprises adding $NaClO_2$ to an aqueous system such that it is present in an amount of at least 1 ppm, for example at least: 2 ppm; 3 ppm; 4 ppm or 5 ppm.

Suitably, the method comprises adding $NaClO_2$ to an aqueous system such that it is present in an amount of greater than 5 ppm. Suitably, the method comprises adding $NaClO_2$ to an aqueous system such that it is present in an amount of at least 10 ppm. Suitably, the method comprises adding $NaClO_2$ to an aqueous system such that it is present in an amount of at least: 15 ppm, for example at least: 20 ppm; 25 ppm; 30 ppm; 35 ppm or 40 ppm. The method may comprise adding $NaClO_2$ to an aqueous system such that it is present in an amount of at least 50 ppm, for example at least: 60 ppm; 70 ppm; 80 ppm; 90 ppm or 100 ppm. The method may comprise adding $NaClO_2$ to an aqueous system such that it is present in an amount of at least 150 ppm, for example at least: 200 ppm; 250 ppm; or 300 ppm.

Suitably, the method comprises adding $NaClO_2$ to an aqueous system such that it is added in an amount of not more than 500 ppm. Suitably, the method comprises adding $NaClO_2$ to an aqueous system such that it is added in an amount of not more than 400 ppm; for example not more than 300 ppm. The method may comprise adding $NaClO_2$ to an aqueous system such that it is added in an amount of not more than 200 ppm, for example not more than 100 ppm.

Suitably, the method comprises adding $NaClO_2$ to an aqueous system such that it is present in an amount of not more than 500 ppm. Suitably, the method comprises adding $NaClO_2$ to an aqueous system such that it is present in an amount of not more than 400 ppm; for example not more than 300 ppm. The method may comprise adding $NaClO_2$ to an aqueous system such that it is present in an amount of not more than 200 ppm, for example not more than 100 ppm.

Suitably, the method comprises adding $NaClO_2$ to an aqueous system to provide a treated aqueous system comprising $NaClO_2$ in an amount of 1 to 500 ppm, for example 5 to 400 ppm. The method may comprise adding $NaClO_2$ to an aqueous system to provide a treated aqueous system comprising NaClO$_2$ in an amount of 10 to 300 ppm, for example 10 to 100 ppm.

Suitably the method comprises adding compound (a) and compound (b) to an aqueous system in a weight ratio of compound (a):compound (b) of from 10:1 to 1:60, for example from 5:1 to 1:50.

The method may comprise adding compound (a) and compound (b) to an aqueous system in a weight ratio of compound (a):compound (b) of from 2:1 to 1:10, for example from 1.5:1.0 to 1.0:5.0.

As used herein, all ratios are weight ratios unless stated otherwise.

Suitably the method comprises adding compound (a) and compound (b) to an aqueous system in a ratio of at least 1:60, for example at least 1:5.

Suitably the method comprises adding compound (a) and compound (b) to an aqueous system in a ratio of no more than 10:1, for example no more than 2:1.

Suitably the method comprises adding compound (a) and compound (b) to an aqueous system in a ratio of from 1.0:1.0 to 1.0:2.0, for example 1.0:1.5.

Suitably the method comprises adding compound (a) and compound (b) to an aqueous system in a ratio of from 1.0:3.0 to 1.0:4.0, for example 1.0:3.3.

Suitably the method comprises adding compound (a) and compound (b) to an aqueous system in a ratio of from 1.0:1.0 to 2.0:1.0, for example 1.3:1.0.

Suitably the method comprises adding compound (a) and compound (b) to an aqueous system in a ratio of from 1.0:1.0 to 1.0:2.0; for example 1.0:1.6.

The method may comprise adding a combination of phosphonium compounds (a) to an aqueous system. Suitably, the method comprises adding a single type of phosphonium compound (a) to an aqueous system.

Suitably, the method employs a phosphonium compound (a) having formula:

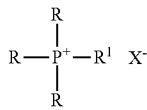

wherein each R is independently a C$_1$-C$_6$ alkyl group which is unsubstituted or substituted by a cyano, hydroxyl, esterified hydroxyl or aryl group;

R$^1$ represents a C$_8$-C$_{18}$ alkyl group which is substituted or unsubstituted; and X represents either chlorine or bromine.

Suitably, each R is a C$_1$-C$_6$ alkyl group. Suitably, each R is a C$_3$-C$_5$ alkyl group. Suitably each R is a butyl group.

Suitably R$^1$ represents a C$_8$-C$_{18}$ alkyl group. Suitably, R1 is a C$_{12}$-C$_{16}$ alkyl group. Suitably, R$^1$ is a tetradecyl group.

Suitably, X is chlorine.

Suitably, the method employs a phosphonium compound (a) which is a phosphonium chloride.

Suitably, the method comprises treating an aqueous system such that phosphonium chloride comprises greater than 50% of the total phosphonium compound(s) added to the aqueous system. Suitably, the method comprises treating an aqueous system such that phosphonium chloride comprises greater than 90% of the total phosphonium compound(s) added to the aqueous system, for example 99% or greater.

Suitably, the method comprises treating an aqueous system such that phosphonium chloride comprises greater than 50% of the total phosphonium compound(s) present in the aqueous system. Suitably, the method comprises treating an aqueous system such that phosphonium chloride comprises greater than 90% of the total phosphonium compound(s) present in the aqueous system, for example 99% or greater.

Suitably, the method employs a phosphonium chloride as the only phosphonium compound (a).

Suitably, the method comprises adding tri n-butyl n-tetradecyl phosphonium chloride (hereafter "TTPC") to the aqueous system. Suitably, the phosphonium compound (a) is TTPC.

Suitably, the method comprises adding TTPC to an aqueous system in an amount of at least 0.1 parts per million (ppm).

Suitably, the method comprises adding TTPC to an aqueous system to provide a treated aqueous system comprising TTPC in an amount of at least 0.1 parts per million (ppm).

Suitably, the method comprises adding TTPC to an aqueous system such that it is added in an amount of at least 0.2 ppm. Suitably, the method comprises adding TTPC to an aqueous system such that it is added in an amount of at least 0.3 ppm, for example at least: 0.4 ppm; 0.5 ppm; 0.6 ppm; 0.7 ppm; 0.8 ppm; 0.9 ppm; or 1.0 ppm. Suitably, the method comprises adding TTPC to an aqueous system such that it is added in an amount of at least 1 ppm; for example at least 1.5 ppm; 2.0 ppm; 2.5 ppm; 3.0 ppm; 3.5 ppm; 4.0 ppm; 4.5 ppm; 5.0 ppm; 5.5 ppm; or 6.0 ppm. The method may comprise adding TTPC to an aqueous system such that it is added in an amount of at least 6 ppm, for example at least: 7 ppm; 8 ppm; 9 ppm; 10 ppm; 11 ppm; 12 ppm. The method may comprise adding TTPC to an aqueous system such that it is added in an amount of at least 20 ppm, for example at least: 25 ppm; 30 ppm; 35 ppm; 40 ppm; 45 ppm; or 50 ppm.

Suitably, the method comprises adding TTPC to an aqueous system such that it is present in an active amount of at least 0.2 ppm. Suitably, the method comprises adding TTPC to an aqueous system such that it is present in an active amount of at least 0.3 ppm, for example at least: 0.4 ppm; 0.5 ppm; 0.6 ppm; 0.7 ppm; 0.8 ppm; 0.9 ppm; or 1.0 ppm. Suitably, the method comprises adding TTPC to an aqueous system such that it is present in an active amount of at least 1 ppm; for example at least 1.5 ppm; 2.0 ppm; 2.5 ppm; 3.0 ppm; 3.5 ppm; 4.0 ppm; 4.5 ppm; 5.0 ppm; 5.5 ppm; or 6.0 ppm. The method may comprise adding a TTPC to an aqueous system such that it is present in an active amount of at least 6 ppm, for example at least: 7 ppm; 8 ppm; 9 ppm; 10 ppm; 11 ppm; 12 ppm. The method may comprise adding TTPC to an aqueous system such that it is present in an active amount of at least 20 ppm, for example at least: 25 ppm; 30 ppm; 35 ppm; 40 ppm; 45 ppm; or 50 ppm.

Suitably, the method comprises adding TTPC to an aqueous system to provide a treated aqueous system comprising TTPC in an amount of 1 to 20 ppm, for example 1 to 15 ppm. Suitably, the method comprises adding TTPC to an aqueous system to provide a treated aqueous system comprising TTPC in an amount of 1 to 10 ppm, for example 2 to 8 ppm, for example 5 to 7 ppm. Suitably, the method comprises adding TTPC to an aqueous system to provide a treated aqueous system comprising TTPC in an amount of 5 to 15 ppm, for example 10 to 14 ppm, for example 11 to 13 ppm.

Suitably, the method comprises adding TTPC to an aqueous system in an amount of not more than 250 ppm, for example not more than 125 ppm.

Suitably, the method may comprise adding TTPC to an aqueous system in an amount of not more than 100 ppm, for example not more than 50 ppm. Suitably, the method comprises adding TTPC to an aqueous system such that it is added in an amount of not more than 40 ppm, for example not more than 35 ppm. The method may comprise adding TTPC to an aqueous system such that it is added in an amount of not more than 30 ppm, for example not more than; 25 ppm; 20 ppm. The method may comprise adding TTPC to an aqueous system such that it is added in an amount of not more than 15 ppm, for example not more than 10 ppm.

Suitably, the method comprises adding TTPC to an aqueous system to provide a treated aqueous system comprising TTPC in an active amount of not more than 250 ppm, for example not more than 125 ppm.

Suitably, the method comprises adding TTPC to an aqueous system to provide a treated aqueous system comprising TTPC in an active amount of not more than 100 ppm, for example not more than 50 ppm. Suitably, the method comprises adding TTPC to an aqueous system such that it is present in an active amount of not more than 40 ppm, for example not more than 35 ppm. The method may comprise adding a TTPC to an aqueous system such that it is present in an amount of not more than 30 ppm, for example not more than; 25 ppm; 20 ppm; 15 ppm; 10 ppm; or 5 ppm.

Suitably, the method comprises adding TTPC to an aqueous system to provide a treated aqueous system comprising TTPC in an amount of 5.5 to 7.0 ppm, for example 6.0 to 6.5 ppm, for example 6.25 ppm. Suitably, the method comprises adding TTPC to an aqueous system to provide a treated aqueous system comprising TTPC in an amount of 10 to 15 ppm, for example 12 to 13 ppm for example 12.5 ppm.

Suitably, the method comprises adding an aqueous composition containing the phosphonium compound (a) to the aqueous system. Suitably, the method comprises adding an aqueous composition of TTPC to the aqueous system. The method may comprise adding an aqueous composition comprising 5% by weight of TTPC to the aqueous system. A suitable composition containing TTPC is available from BWA Water Additives and is sold under the trade name Bellacide 355 (an aqueous composition of TTPC and water consisting of water and 5% by weight of TTPC). The method may comprise adding an aqueous composition comprising 50% by weight of TTPC to the aqueous system. A suitable composition containing TTPC is available from BWA Water Additives and is sold under the trade name Bellacide 350 (an aqueous composition of TTPC and water consisting of water and 50% by weight of TTPC).

Suitably, the method comprises treating an aqueous system such that TTPC comprises greater than 50% of the total phosphonium compound(s) added to the aqueous system. Suitably, the method comprises treating an aqueous system such that TTPC comprises greater than 90% of the total phosphonium compound(s) added to the aqueous system, for example 99% or greater.

Suitably, the method comprises treating an aqueous system such that TTPC comprises greater than 50% of the total phosphonium compound(s) present in the aqueous system. Suitably, the method comprises treating an aqueous system such that TTPC comprises greater than 90% of the total phosphonium compound(s) present in the aqueous system, for example 99% or greater.

Suitably, the method employs TTPC as the only phosphonium compound (a).

The method may comprise adding a combination of compounds of type (b) to an aqueous system. Suitably, the method comprises adding a single compound of type (b) to an aqueous system.

Suitably, the method employs $NaClO_2$ as the only compound of type (b).

Suitably, the method comprises treating an aqueous system such that $NaClO_2$ comprises greater than 50% of the compounds of type (b) added to the aqueous system. Suitably, the method comprises treating an aqueous system such that $NaClO_2$ comprises greater than 90% of the total of compounds of type (b) added to the aqueous system, for example 99% or greater.

Suitably, the method employs a beneficial combination of compounds (a) and (b).The method may employ a synergistic mixture of compounds (a) and (b). Suitably, by "synergistic mixture" it is meant that the mixture of compounds (a) and (b) has a synergistic effect on the inhibition of growth of one or more biological organisms, preferably micro-organisms such as bacteria, fungi and/or algae and/or has a synergistic effect on reducing the number of one or more biological organisms, preferably micro-organisms such as bacteria, fungi and/or algae.

Suitably the method comprises adding TTPC and $NaClO_2$ to an aqueous system in a weight ratio of TTPC:$NaClO_2$ of from 10:1 to 1:60, for example from 5:1 to 1:50.

The method may comprise adding TTPC and $NaClO_2$ to an aqueous system in a weight ratio of TTPC:$NaClO_2$ of from 2:1 to 1:10, for example from 1.5:1.0 to 1.0:5.0.

Suitably, the method comprises adding TTPC and $NaClO_2$ to an aqueous system such that TTPC is added in an amount of 20 ppm or less and such that TTPC and $NaClO_2$ are added in a weight ratio of TTPC:$NaClO_2$ of from 2:1 to 1:10.

Suitably, the method comprises adding TTPC and $NaClO_2$ to an aqueous system such that TTPC is added in an amount of 15 ppm or less and such that TTPC and $NaClO_2$ are added in a weight ratio of TTPC:$NaClO_2$ of from 2:1 to 1:10.

Suitably, the method comprises adding TTPC and $NaClO_2$ to an aqueous system such that TTPC is added in an amount of 10 ppm or less and such that TTPC and $NaClO_2$ are added in a weight ratio of TTPC:$NaClO_2$ of from 2:1 to 1:10.

Suitably, the method comprises adding TTPC and $NaClO_2$ to an aqueous system such that TTPC is added in an amount of 1 to 8 ppm and such that TTPC and $NaClO_2$ are added in a weight ratio of TTPC:$NaClO_2$ of from 1.5:1.0 to 1.0:5.0.

Suitably, the method comprises adding TTPC and $NaClO_2$ to an aqueous system such that TTPC is added in an amount of 20 ppm or less and such that TTPC and $NaClO_2$ are added in a weight ratio of TTPC:$NaClO_2$ of from 2:1 to 1:10.

Suitably, the method comprises treating an oil and gas field water system having a total dissolved solids (TDS) of 30,000 mg l-1 or greater and the method comprises adding TTPC and $NaClO_2$ such that TTPC is added in an amount of 20 ppm or less and such that TTPC and $NaClO_2$ are added in a weight ratio of TTPC:$NaClO_2$ of from 2:1 to 1:10.

The method may comprise adding compound (a) and compound (b) to the aqueous system such that the aqueous system comprises a synergistic mixture of compounds (a) and (b).

The method may comprise adding compound (a) and compound (b) as a mixture to the aqueous system. The method may comprise adding a biocidal composition comprising compound (a) and compound (b) to the aqueous system. The method may comprise mixing compound (a) and compound (b) and adding the mixture to the aqueous system. Suitably, the method comprises adding compound (a) and compound (b) separately to the aqueous system and allowing or causing them to mix within the aqueous system.

Where the method comprises mixing compound (a) and compound (b) and adding the mixture to the aqueous system and/or adding compound (a) and compound (b) separately to the aqueous system and allowing or causing them to mix within the aqueous system, then compounds (a) and (b) are preferably used in the form of aqueous compositions.

Suitably, compound (a) is used in the form of an aqueous composition comprising between 1% and 90% by weight of compound (a), for example between 1% and 60% by weight. Suitably, compound (a) is used in the form of an aqueous composition comprising between 1% and 10% by weight of compound (a), for example 5% by weight.

Suitably, compound (b) is used in the form of an aqueous composition comprising between 1% and 95% by weight of compound (b), for example between 10% and 90% by weight. Suitably, compound (b) is used in the form of an aqueous composition comprising between 50% and 90% by weight of compound (b), for example 80% by weight.

The method may comprise adding a stabilising agent to the aqueous system. The method may comprise adding a stabilised treatment agent to the aqueous system. The method may comprise adding a treatment agent comprising compound (a) or (b) and a stabiliser.

The method may comprise a method of treating an industrial water system. The method may comprise treating a cooling water system. The method may comprise treating a pulping and/or papermaking water system. The method may comprise treating an oil and/or gas field water system. The method may comprise treating an aqueous system to control the growth of bacterial and/or algal micro-organisms contained therein and/or which may become entrained in said system.

It has been found that the compositions and methods of utilisation of the present invention may in particular be efficacious in controlling acid producing facultative anaerobic bacteria and hydrogen sulphide producing anaerobic bacteria which may populate aqueous systems.

Surprisingly, it has been found that when compound (a) and compound (b) are combined, the resulting combination may pose a higher degree of biocidal activity in an aqueous system than that of the individual compounds used alone. Because of the enhanced activity of the combination of treatment agent compounds, it may be possible for the total quantity of treatment agent added to an aqueous system to be reduced in comparison to a system using only one of said treatment agent compounds. In addition, the high degree of biocidal activity which is provided by each of the treatment agent compounds may be exploited without use of higher concentrations of each. The combination of TTPC and NaClO$_2$ may be particularly effective. The composition may also be surprisingly effective in systems having high total dissolved solids (TDS).

It has been found that the compositions and methods of utilisation of the present invention may in particular be efficacious in controlling the facultative anaerobic bacterium Enterobacter aerogenes and/or the anaerobic bacterium *Desulfovibrio vulgaris*, which may populate aqueous systems.

Surprisingly, the present inventors have found that mixtures of compound (a) and compound (b), such as mixtures of tri-n-butyl n-tetradecyl phosphonium chloride (TTPC) and NaClO$_2$, are especially efficacious in controlling the growth of micro-organisms such as bacterial and algal microbes in aqueous systems comprising dissolved solids and there is an unexpected synergistic relationship.

It has been found that compositions of compounds (a) and compound (b) may be unexpectedly effective against facultative anaerobes and anaerobes and may have a marked synergy at short contact times. For example, NaClO$_2$ may show no biocidal activity against anaerobes or facultative anaerobes at short contact times but the addition of TTPC may greatly improve performance even though TTPC alone may be of limited effectiveness against anaerobes and may be ineffective against facultative anaerobes at short contact times.

According to a second aspect of the present invention there is provided a method of treating an aqueous system comprising greater than 20,000 mg l$^{-1}$ total dissolved solids (TDS) to inhibit growth of one or more micro-organisms therein and/or to reduce the number of live micro-organisms therein, wherein the method comprises adding treatment agents to said aqueous system and wherein said treatment agents comprise:

(a) TTPC; and
(b) NaClO$_2$.

The method of the second aspect may comprise any feature as described in relation to the first aspect except where such features are mutually exclusive.

According to a third aspect of the present invention there is provided an aqueous system comprising a combination of:
(a) a phosphonium compound; and
(b) a compound having formula:

wherein:
M is a Group I or Group II metal;
X is a halogen; and
n is 1 or 2.

Suitably, M is a Group I metal. Suitably M is sodium.
Suitably, X is bromine or chlorine. Suitably, X is chlorine.
Suitably n is 1.
Suitably, compound (b) is NaClO$_2$.
Suitably, the aqueous system comprises greater than 10,000 mg l$^{-1}$ total dissolved solids (TDS). Suitably, the aqueous system comprises greater than 20,000 mg l$^{-1}$ total dissolved solids (TDS), for example greater than 30,000 mg l$^{-1}$ TDS.

Suitably, compound (a) is TTPC.
Suitably the aqueous system comprises a mixture of water and other constituents. The aqueous system may contain oil. The aqueous system may comprise an oil and water emulsion. The aqueous system may comprise solids. The aqueous system may comprise suspended solids. The aqueous system may comprise high levels of dissolved solids. The aqueous system may comprise one or more salts, for example sodium chloride. Suitably, the aqueous system consists of a body of water. Suitably, the aqueous system consists of a body of water which comprises water and other constituents, for example dissolved solids.

Suitably, the aqueous system comprises an industrial water system. The aqueous system may consist of industrial water. The aqueous system may comprise a cooling water system. The aqueous system may comprise a pulping and papermaking system. The aqueous system may comprise an oil and gas field water system. The aqueous system may comprise a well treatment fluid.

The aqueous system may comprise cooling water. The aqueous system may consist of cooling water, comprising compound (a), compound (b) and optionally other constituents in addition to water. The aqueous system may comprise pulping and papermaking water. The aqueous system may consist of pulping and papermaking water, comprising compound (a), compound (b) and optionally other constituents in addition to water. The aqueous system may comprise oil and gas field water. The aqueous system may consist of oil and gas field water, comprising compound (a), compound (b) and optionally other constituents in addition to water. The aqueous system may comprise well treatment fluid. The aqueous system may consist of well treatment fluid, comprising compound (a), compound (b) and optionally other constituents in addition to water.

Suitably, the aqueous system comprises TTPC in an amount of 20 ppm or less and comprises TTPC and NaClO$_2$ in a weight ratio of TTPC:NaClO$_2$ of from 10:1 to 1:60, for example 2:1 to 1:10.

Suitably, the aqueous system comprises an oil and gas field water system having a total dissolved solids (TDS) of 30,000 mg l$^{-1}$ or greater and comprises TTPC and NaClO$_2$ such that TTPC is present in an amount of 20 ppm or less and such that TTPC and NaClO$_2$ are present in a weight ratio of TTPC:NaClO$_2$ of from 2:1 to 1:10.

The aqueous system of the third aspect may comprise any feature as described in relation to one or more of the first and/or second aspects except where such features are mutually exclusive.

According to a fourth aspect of the present invention there is provided a method of inhibiting or preventing the growth of one or more micro-organisms in a water based liquid, wherein the method comprises adding treatment agents to said water based liquid and wherein said treatment agents comprise:
(a) a phosphonium compound; and
(b) a compound having formula:

$$M(XO_2)_n$$

wherein:
M is a Group I or Group II metal;
X is a halogen; and
n is 1 or 2.
Suitably, M is a Group I metal. Suitably M is sodium.
Suitably, X is bromine or chlorine. Suitably, X is chlorine.
Suitably n is 1.
Suitably, compound (b) is NaClO$_2$.
Suitably, the water based liquid comprises greater than 10,000 mg l$^{-1}$ total dissolved solids (TDS). Suitably, the water based liquid comprises greater than 20,000 mg l$^{-1}$ total dissolved solids (TDS), for example greater than 30,000 mg l$^{-1}$ TDS.
Suitably, compound (a) is TTPC.
Suitably the water based liquid comprises a mixture of water and other constituents. The water based liquid may contain oil. The water based liquid may comprise an oil and water emulsion. The water based liquid may comprise solids. The water based liquid may comprise suspended solids. The water based liquid may comprise high levels of dissolved solids. The water based liquid may comprise one or more salts, for example sodium chloride.

The water based liquid may comprise industrial water. The water based liquid may consist of industrial water which may comprise water and other constituents. The water based liquid may comprise cooling water. The water based liquid may consist of cooling water which may comprise water and other constituents. The water based liquid may comprise pulping and papermaking water. The water based liquid may consist of pulping and papermaking water which may comprise water and other constituents. The water based liquid may comprise oil and gas field water. The water based liquid may consist of oil and gas field water which may comprise water and other constituents. The water based liquid may comprise a well treatment fluid. The water based liquid may consist of well treatment fluid which may comprise water and other constituents.

Suitably, the method comprises treating industrial water to inhibit growth of one or more micro-organisms therein and/or to reduce the number of live micro-organisms therein. The method may comprise treating cooling water to inhibit growth of one or more micro-organisms therein and/or to reduce the number of live micro-organisms therein. The method may comprise treating pulping and papermaking water to inhibit growth of one or more micro-organisms therein and/or to reduce the number of live micro-organisms therein. The method may comprise treating oil and gas field water to inhibit growth of one or more micro-organisms therein and/or to reduce the number of live micro-organisms therein. The method may comprise treating a well treatment fluid to inhibit growth of one or more micro-organisms therein and/or to reduce the number of live micro-organisms therein.

Suitably, the method comprises adding TTPC and NaClO$_2$ to a water based liquid such that TTPC is added in an amount of 20 ppm or less and such that TTPC and NaClO$_2$ are added in a weight ratio of TTPC:NaClO$_2$ of from 10:1 to 1:60, for example from 2:1 to 1:10.

Suitably, the method comprises treating an oil and gas field water system having a total dissolved solids (TDS) of 30,000 mg l-1 or greater and wherein the method comprises adding TTPC and NaClO$_2$ such that TTPC is added in an amount of 20 ppm or less and such that TTPC and NaClO$_2$ are added in a weight ratio of TTPC:NaClO$_2$ of from 2:1 to 1:10.

The method of the fourth aspect may comprise any feature as described in relation to one or more of the first and/or second and/or third aspects except where such features are mutually exclusive.

According to a fifth aspect of the present invention there is provided a water based liquid incorporating a combination of:
(a) a phosphonium compound; and
(b) a compound having formula:

$$M(XO_2)_n$$

wherein:
M is a Group I or Group II metal;
X is a halogen; and
n is 1 or 2.
Suitably, M is a Group I metal. Suitably M is sodium.
Suitably, X is bromine or chlorine. Suitably, X is chlorine.
Suitably n is 1.
Suitably, compound (b) is NaClO$_2$.
Suitably, the water based liquid comprises greater than 10,000 mg l$^{-1}$ total dissolved solids (TDS). Suitably, the water based liquid comprises greater than 20,000 mg l$^{-1}$ total dissolved solids (TDS), for example greater than 30,000 mg l$^{-1}$ TDS.
Suitably, compound (a) is TTPC.
Suitably the water based liquid comprises a mixture of water and other constituents. The water based liquid may contain oil. The water based liquid may comprise an oil and water emulsion. The water based liquid may comprise solids. The water based liquid may comprise suspended solids. The water based liquid may comprise high levels of dissolved solids. The water based liquid may comprise one or more salts, for example sodium chloride.

The water based liquid may comprise industrial water. The water based liquid may consist of industrial water, comprising compound (a), compound (b) and optionally other constituents in addition to water. The water based liquid may comprise cooling water. The water based liquid may consist of cooling water, comprising compound (a), compound (b) and optionally other constituents in addition to water. The water based liquid may comprise pulping and papermaking water. The water based liquid may consist of pulping and papermaking water, comprising compound (a), compound (b) and optionally other constituents in addition to water. The water based liquid may comprise oil and gas field water. The water based liquid may comprise oil and gas field water. The water based liquid may consist of oil and gas field water, comprising compound (a), compound (b) and optionally other constituents in addition to water. The water based liquid may comprise a well treatment fluid. The water based liquid may consist of well treatment fluid, comprising compound (a), compound (b) and optionally other constituents in addition to water.

Suitably, the water based liquid comprises TTPC in an amount of 20 ppm or less and comprises TTPC and $NaClO_2$ in a weight ratio of TTPC:$NaClO_2$ of from 10:1 to 1:60, for example 2:1 to 1:10.

Suitably, the water based liquid comprises an oil and gas field water system having a total dissolved solids (TDS) of 30,000 mg $l^{-1}$ or greater and comprises TTPC and $NaClO_2$ such that TTPC is present in an amount of 20 ppm or less and such that TTPC and $NaClO_2$ are present in a weight ratio of TTPC:$NaClO_2$ of from 2:1 to 1:10.

The water based liquid of the fifth aspect may comprise any feature as described in relation to one or more of the first and/or second and/or third and/or fourth aspects except where such features are mutually exclusive.

According to a sixth aspect of the present invention there is provided a biocidal composition comprising a combination of:
(a) a phosphonium compound; and
(b) a compound having formula:

$M(XO_2)_n$ wherein:
M is a Group I or Group II metal;
X is a halogen; and
n is 1 or 2.
Suitably, M is a Group I metal. Suitably M is sodium.
Suitably, X is bromine or chlorine. Suitably, X is chlorine.
Suitably n is 1.
Suitably, compound (b) is $NaClO_2$.
Suitably, compound (a) is TTPC.
Suitably, the biocidal composition comprises one or more compounds of type (a), one or more compounds of type (b) and water in a combined amount of at least 50% by weight of the biocidal composition. Suitably, the biocidal composition comprises compounds (a) and (b) and water in a combined amount of at least 90% by weight of the biocidal composition. Suitably, the biocidal composition comprises compounds (a) and (b) and water in a combined amount of at least 95% by weight of the biocidal composition, for example at least 99% by weight. Suitably, the biocidal composition consists of compounds (a) and (b) and water.

Suitably, the biocidal composition comprises compounds (a) and (b) in a weight ratio of (a):(b) of from 10:1 to 1:60, for example from 2:1 to 1:10.

The biocidael composition of the sixth aspect may comprise any feature as described in relation to one or more of the first and/or second and/or third and/or fourth and/or fifth aspects except where such features are mutually exclusive.

DETAILED DESCRIPTION OF PREFERRED EMBODIMENTS

The present invention will now be illustrated by way of example with reference to the following preferred embodiments.

EXAMPLES

Aqueous systems inoculated with anaerobe and facultative anaerobe culture and having a total dissolved solids (TDS) concentration of 30,000 mg $l^{-1}$ were prepared and treated with treatment agents comprising: (a) tri n-butyl n-tetradecyl phosphonium chloride (TTPC) and (b) $NaClO_2$.

TTPC was used in the form of Bellacide 350, an aqueous composition of TTPC and water consisting of water and 50% by weight of TTPC available from BWA Water Additives.

$NaClO_2$ was used in the form of Reagan Grade Sodium Chlorite, an 80% aqueous solution of $NaClO_2$ available from Amresco.

A suspension of *Desulfovibrio vulgaris* plus*Enterobacter aerogenes* bacteria containing from $1\times10^5$ to $1\times10^6$ cells/mL was prepared in sterile pH 8 phosphate buffer containing sodium chloride to give the desired total dissolved solids (TDS) concentration. Aliquots of this suspension were dosed with the indicated concentrations of the compounds (a) and (b) with the concentrations being measured as ppm active. The mixtures were allowed to stand at room temperature. At the designated contact times, each mixture was sampled to determine the total number of viable cells of both *Desulfovibrio vulgaris* and *Enterobacter aerogenes* by serial 10-fold dilution into API RP 38 media vials and anaerobic acid producing media vials, respectively. The vials were incubated at 37° C. for 72 hours. Results were recorded as $log_{10}$ reduction in the viable count versus the control.

The efficacy of the treatment agents was evaluated by measuring the $Log_{10}$ Reduction of the anaerobic bacterium *Desulfovibrio vulgaris* and the facultative anaerobic bacterium *Enterobacter aerogenes* after contact times of 1 hour, 4 hours and 24 hours as detailed in Table 1. For TTPC the stated ppm value relates to the amount of TTPC added (active). For $NaClO_2$ the stated ppm relates to the amount of $NaClO_2$ added (active).

TABLE 1

| Example | pH | TDS (mg $l^{-1}$) | Contat time (hours) | Treatment agent (ppm active) TTPC | $NaClO_2$ | $Log_{10}$ Reduction Anaerobes* | $Log_{10}$ Reduction Facultative Anaerobes** |
|---|---|---|---|---|---|---|---|
| 1 (comparative) | 8.0 | 30,000 | 1 | 6.25 | — | 2 | 0 |
| 2 (comparative) | 8.0 | 30,000 | 1 | 12.5 | — | 5 | 3 |
| 3 (comparative) | 8.0 | 30,000 | 1 | — | 10 | 0 | 0 |

TABLE 1-continued

| Example | pH | TDS (mg l$^{-1}$) | Contat time (hours) | Treatment agent (ppm active) | | Log$_{10}$ Reduction Anaerobes* | Log$_{10}$ Reduction Facultative Anaerobes** |
|---|---|---|---|---|---|---|---|
| | | | | TTPC | NaClO$_2$ | | |
| 4 (comparative) | 8.0 | 30,000 | 1 | — | 20 | 0 | 0 |
| 5 | 8.0 | 30,000 | 1 | 6.25 | 10 | 5 | 1 |
| 6 | 8.0 | 30,000 | 1 | 6.25 | 20 | 5 | 1 |
| 7 | 8.0 | 30,000 | 1 | 12.5 | 10 | 5 | 4 |
| 8 | 8.0 | 30,000 | 1 | 12.5 | 20 | 5 | 6 |
| 9 (comparative) | 8.0 | 30,000 | 4 | 6.25 | — | 5 | 3 |
| 10 (comparative) | 8.0 | 30,000 | 4 | 12.5 | — | 5 | 4 |
| 11 (comparative) | 8.0 | 30,000 | 4 | — | 10 | 0 | 0 |
| 12 (comparative) | 8.0 | 30,000 | 4 | — | 20 | 1 | 0 |
| 13 | 8.0 | 30,000 | 4 | 6.25 | 10 | 5 | 6 |
| 14 | 8.0 | 30,000 | 4 | 6.25 | 20 | 5 | 6 |
| 15 | 8.0 | 30,000 | 4 | 12.5 | 10 | 5 | 6 |
| 16 | 8.0 | 30,000 | 4 | 12.5 | 20 | 5 | 6 |
| 17 (comparative) | 8.0 | 30,000 | 24 | 6.25 | — | 5 | 5 |
| 18 (comparative) | 8.0 | 30,000 | 24 | 12.5 | — | 5 | 6 |
| 19 (comparative) | 8.0 | 30,000 | 24 | — | 10 | 4 | 0 |
| 20 (comparative) | 8.0 | 30,000 | 24 | — | 20 | 4 | 0 |
| 21 | 8.0 | 30,000 | 24 | 6.25 | 10 | 5 | 6 |
| 22 | 8.0 | 30,000 | 24 | 6.25 | 20 | 5 | 6 |
| 23 | 8.0 | 30,000 | 24 | 12.5 | 10 | 5 | 6 |
| 24 | 8.0 | 30,000 | 24 | 12.5 | 20 | 5 | 6 |

*5 = complete kill for anaerobes
**6 = complete kill for facultative anaerobes

The results show that surprisingly, despite NaClO$_2$ being ineffective alone against anaerobes at short contact times and of limited effectiveness at longer contact times the combination of TTPC and NaClO$_2$ was very effective against anaerobes, achieving complete kill (5 log reduction) at one hour contact times.

The results with facultative anaerobes also show unexpected efficacy of the combination of TTPC and NaClO$_2$ with the combination achieving complete kill (6 log reduction) at 4 hours contact time.

It is particularly surprising that low levels of TTPC are effective with low levels of NaClO$_2$. Accordingly, it will be appreciated that combining TTPC and NaClO$_2$ may allow for less TTPC to be used to achieve kill of facultative anaerobes and anaerobes compared to TTPC alone. It will also be appreciated that combining TTPC and NaClO$_2$ may allow for complete kill of facultative anaerobes and anaerobes using TTPC and NaClO$_2$ at certain contact times which may not be achievable if using TTPC only.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A method of treating an aqueous system to inhibit growth of one or more micro-organisms therein and/or to reduce the number of live micro-organisms therein, wherein the method comprises adding treatment agents to an aqueous system and wherein said treatment agents consists of:
   (a) a phosphonium component comprising tri-n-butyl n-tetradecyl phosphonium chloride (TTPC);
   (b) a compound having a formula of:

$$M(XO_2)_n$$

wherein:
   M is a Group I or Group II metal;
   X is a halogen; and
   n is 1 or 2; and
   (c) optionally water.

2. The method according to claim 1, wherein compound (b) is NaClO$_2$.

3. The method according to claim 1, wherein compound (b) is NaClO$_2$ and wherein the aqueous system comprises water in an amount of up to 99% by weight.

4. The method according to claim 1, wherein the method comprises adding compound (a) to the aqueous system in an amount of no more than 20 ppm.

5. The method according to claim 1, wherein the method comprises adding compound (b) to the aqueous system in an amount of no more than 300 ppm.

6. The method according to claim 1, wherein the method comprises adding compound (a) and compound (b) to the aqueous system in a combined amount of from 0.1 to 300 ppm.

7. The method according to claim 1, wherein the aqueous system comprises salts in an amount of 10,000 mg l$^{-1}$ or greater.

8. The method according to claim 1, wherein the aqueous system has a total dissolved solids (TDS) of 30,000 mg l$^{-1}$ or greater.

9. The method according to claim 1, wherein the method comprises adding compound (a) and compound (b) to the aqueous system in a weight ratio of from 10:1 to 1:60.

10. The method according to claim 1, wherein the method comprises treating the aqueous system to inhibit growth of anaerobic bacteria and to reduce the number of live anaerobic bacteria therein.

11. The method according to claim 1, wherein the method comprises treating the aqueous system to inhibit growth of aerobic bacteria and to reduce the number of live aerobic bacteria therein.

12. The method according to claim 1, wherein the method comprises treating the aqueous system to inhibit growth of facultative anaerobic bacteria and to reduce the number of live facultative anaerobic bacteria therein.

13. The method according to claim 1, wherein the method comprises adding TTPC and NaClO$_2$ to the aqueous system, wherein the TTPC is added in an amount of 20 ppm or less and the TTPC and NaClO$_2$ are added in a weight ratio of TTPC:NaClO$_2$ of from 2:1 to 1:10.

14. The method according to claim 1, wherein the aqueous system is an oil and gas field water system having a total dissolved solids (TDS) of 30,000 mg l$^{-1}$ or greater and wherein the method comprises adding TTPC and NaClO$_2$ to the aqueous system, wherein the TTPC is added in an amount of 20 ppm or less and the TTPC and NaClO$_2$ are added in a weight ratio of TTPC:NaClO$_2$ of from 2:1 to 1:10.

15. The method according to claim 1, wherein the aqueous system comprises oil in an amount of at least 1% by weight.

16. The method according to claim 1, wherein the method comprises treating industrial water.

17. The method according to claim 1, wherein the aqueous system is an oil and gas field water system having a total dissolved solids (TDS) of 30,000 mg l$^{-1}$ or greater, wherein the oil and gas field water system comprises oil in an amount of at least 1% by weight, wherein compound (b) is NaClO$_2$, wherein the TTPC is added in an amount of 20 ppm or less and the TTPC and NaClO$_2$ are added in a weight ratio of TTPC:NaClO$_2$ of from 2:1 to 1:10, and wherein the method comprises treating the aqueous system to inhibit growth of *Desulfovibrio vulgaris* bacteria and *Enterobacter aerogenes* bacteria therein and/or to reduce the number of live *Desulfovibrio vulgaris* bacteria and *Enterobacter aerogenes* bacteria therein.

18. The method according to claim 1, wherein the aqueous system is an oil and gas field water system having a total dissolved solids (TDS) of 30,000 mg l$^{-1}$ or greater, wherein the oil and gas field water system comprises oil in an amount of at least 1% by weight, wherein compound (b) is NaClO$_2$, and wherein the TTPC is added in an amount of 20 ppm or less and the TTPC and NaClO$_2$ are added in a weight ratio of TTPC:NaClO$_2$ of from 2:1 to 1:10.

19. The method according to claim 1, wherein the method comprises treating the aqueous system to inhibit growth of *Desulfovibrio vulgaris* bacteria and *Enterobacter aerogenes* bacteria therein and/or to reduce the number of live *Desulfovibrio vulgaris* bacteria and *Enterobacter aerogenes* bacteria therein.

20. A method of treating an aqueous system comprising greater than 20,000 mg l$^{-1}$ total dissolved solids (TDS) to inhibit growth of one or more micro-organisms therein and/or to reduce the number of live micro-organisms therein, wherein the method comprises adding treatment agents to said aqueous system and wherein said treatment agents consist of a combination of:
(a) a phosponium component comprising tri-n-butyl n-tetradecyl phosphonium chloride (TTPC);
(b) NaClO$_2$; and
(c) optionally water;
wherein the combination of TTPC and NaClO$_2$ are added to the aqueous system in amounts configured to inhibit growth of the one or more micro-organisms therein and/or to reduce the number of live micro-organisms therein.

21. The method according to claim 20, wherein the method comprises treating the aqueous system to inhibit growth of *Desulfovibrio vulgaris* bacteria and *Enterobacter aerogenes* bacteria therein and/or to reduce the number of live *Desulfovibrio vulgaris* bacteria and *Enterobacter aerogenes* bacteria therein.

22. An aqueous system comprising treatment agents consisting of a combination of:
(a) a phosponium component comprising tri-n-butyl n-tetradecyl phosphonium chloride (TTPC); and
(b) a compound having a formula of:

$$M(XO_2)_n$$

wherein:
M is a Group I or Group II metal;
X is a halogen; and
n is 1 or 2; and
(c) optionally water.

23. A method of inhibiting or preventing the growth of one or more micro-organisms in a water based liquid, wherein the method comprises adding treatment agents to said water based liquid and wherein said treatment agents consist of:
(a) a phosponium component comprising tri-n-butyl n-tetradecyl phosphonium chloride (TTPC); and
(b) a compound having a formula of:

$$M(XO_2)_n$$

wherein:
M is a Group I or Group II metal;
X is a halogen; and
n is 1 or 2; and
(c) optionally water.

24. The method according to claim 23, wherein the method comprises inhibiting or preventing the growth of *Desulfovibrio vulgaris* bacteria and *Enterobacter aerogenes* bacteria in the water based liquid.

25. A water based liquid consisting of:
(a) a phosponium component comprising tri-n-butyl n-tetradecyl phosphonium chloride (TTPC); and
(b) a compound having a formula of:

$$M(XO_2)_n$$

wherein:
M is a Group I or Group II metal;
X is a halogen; and
n is 1 or 2; and
(c) optionally water.

26. A biocidal composition consisting of a combination of:
(a) a phosponium component comprising tri-n-butyl n-tetradecyl phosphonium chloride (TTPC); and
(b) a compound having a formula of:

$$M(XO_2)_n$$

wherein:
   M is a Group I or Group II metal;
   X is a halogen; and
   n is 1 or 2; and
(c) optionally water.

* * * * *